United States Patent [19]

Davis et al.

[11] 4,002,686
[45] Jan. 11, 1977

[54] METHOD OF PREPARING PRIMARY ALIPHATIC MERCAPTANS

[75] Inventors: Kirk Emerson Davis, Euclid; Emil Thomas Wierber, Mayfield Village, both of Ohio

[73] Assignee: The Lubrizol Corporation, Cleveland, Ohio

[22] Filed: Aug. 5, 1975

[21] Appl. No.: 602,037

[52] U.S. Cl. .................... 260/609 R; 260/609 D
[51] Int. Cl.[2] ............. C07C 149/08; C07C 148/00
[58] Field of Search .................... 260/609 R, 609 D

[56] References Cited
OTHER PUBLICATIONS

W. Theilheimer; Syn. Method of Org. Chem., vol. 17, pp. 46–47.

*Primary Examiner*—Lewis Gotts
*Assistant Examiner*—D. R. Phillips
*Attorney, Agent, or Firm*—James W. Adams, Jr.; William H. Pittman

[57] ABSTRACT

Primary aliphatic (preferably alkyl) mercaptans are prepared by heating a phosphorus-sulfur compound, preferably a primary aliphatic phosphorodithioic acid, with a basic nitrogen compound. The preferred basic nitrogen compounds are amines and particularly aliphatic primary and secondary amines, especially alkylene polyamines.

13 Claims, No Drawings

METHOD OF PREPARING PRIMARY ALIPHATIC MERCAPTANS

This invention relates to a new method for the preparation of primary mercaptans. More particularly, it relates to a method for preparing mercaptans of the formula RSH which comprises heating a composition consisting essentially of at least one of (1) a mixture of a phosphorus-sulfur compound having the formula $(RX)_2PSSR'$, wherein R' is hydrogen or R, each R is individually an aliphatic-based radical with at least one R being a primary radical, and each X is individually oxygen or sulfur, and a basic nitrogen compound, and (2) a salt of said basic nitrogen compound and said phosphorus-sulfur compound, at a temperature sufficient to result in formation of said mercaptan.

(The singular forms "a", "an" and "the", as used herein, include the plural unless the context clearly dictates otherwise. Thus, for example, "a basic nitrogen compound" includes a mixture of such compounds.)

Primary alkyl mercaptans are useful for many purposes well known in the art. Among these are pesticides, defoliants, antioxidants, inhibitors, detergents, ore flotation collectors, polymerization modifiers, odorants, and intermediates for the preparation of such materials as pharmaceuticals and lubricant additives. The methods for the preparation of these mercaptans are, however, not entirely satisfactory since they often involve multiple steps and the use of reactants which are inconvenient or dangerous to handle. For these reasons, alternative methods of preparing these mercaptans are still of interest.

A principal object of the present invention, therefore, is to provide a new method for producing primary alkyl mercaptans and the like.

A further object to provide a method for preparing mercaptans which enables them to be easily recovered in good yield and with a high degree of purity.

Other objects will in part be obvious and will in part appear hereinafter.

As will be apparent from the above summary of the invention, it is based upon the discovery that primary alkyl and similar mercaptans can be recovered from the reaction mixture obtained from certain phosphorus-sulfur compounds and basic nitrogen compounds. The preferred phosphorus-sulfur compounds are phosphorodithioic acids of the formula $(RO)_2PSSH$, wherein R is as previously defined.

The reaction medium is defined alternatively as at least one of a reaction mixture and a salt, since the degree of salt formation will vary with the relative acidic and basic strengths of the acids and nitrogen compounds used. For example, a primary alkyl phosphorodithioic acid is a relatively strong acid, and if it is mixed with a strongly basic amine such as diethylamine, the product will be predominantly a salt. However, a mixture of the same acid with a weakly basic amine such as diphenylamine may produce relatively small quantities of the salt, the main portion of the mixture being free acid and amine. It is difficult to determine the extent of salt formation in any specific acid-nitrogen compound blend and since such extent is not critical from the standpoint of this invention, the invention is defined in terms of both mixtures and salts.

Another suitable class of phosphorus-sulfur compounds are the tetrathiophosphates of the formula $(RS)_3PS$, wherein R is as previously defined. Such tetrathiophosphates may be prepared as described in *J. Gen. Chem. USSR*, 41, 1036 (1971), typically by the reaction of a phosphorodithioic acid with phosphorus pentasulfide.

The relative proportions of phosphorus-sulfur compound and nitrogen compound used in the method of this invention are not critical. In fact, some mercaptan can be produced merely by heating a phosphorodithioic acid alone. However, it has been found that the addition of a basic nitrogen compound to such acid materially increases the yield of said mercaptan. The ratio of equivalents of phosphorus-sulfur compound to nitrogen compound is conveniently between 1:0.05 and 1:5. Preferably, it is between 1:0.1 and 1:4, and maximum yields are obtained when the ratio is between about 1:1 and 1:4. (For the purposes of this invention the equivalent weight of a phosphorus-sulfur compound is its molecular weight divided by the number of phosphorus atoms therein, and the equivalent weight of a basic nitrogen compound is its molecular weight divided by the number of basic nitrogen atoms therein.)

Basic nitrogen compounds which may be used in the method of this invention include, in general, those nitrogen-containing compounds in which the valences of nitrogen are satisfied by hydrogen, amino or hydrocarbon-based radicals. As used herein, the term "hydrocarbon-based radical" denotes a radical having a carbon atom directly attached to the remainder of the molecule (nitrogen in this case) and having predominantly hydrocarbon character within the context of this invention. Such radicals include the following:

1. Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples (all isomers being included) are methyl, ethyl, propyl, butyl, hexyl, octyl, nonyl, decyl, dodecyl, pentadecyl, eicosyl and triacontanyl.

2. Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are halo, nitro, cyano, R'O—,

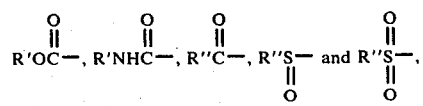

wherein R' may be hydrogen or a hydrocarbon radical and R'' may be a hydrocarbon radical.

3. Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

Terms such as "aliphatic-based radical", "alkyl-based radical" and the like have analogous meanings with respect to aliphatic and alkyl radicals and the like.

As will be apparent from the foregoing, suitable nitrogen compounds include ammonia, amines and hydrazines. The amines may be aliphatic, aromatic, carbocyclic or heterocyclic. They may be primary, secondary or tertiary, although amines containing at least one primary or secondary amino group are preferred in the method of this invention and will be referred to predominantly hereinafter.

Monoamines may be used in the method of this invention, especially primary or secondary monoamines and preferably those in which the hydrocarbon-based radicals are free from acetylenic unsaturation and contain about 1–30, usually about 1–10, carbon atoms. Monoamines containing alkyl-based (i.e., saturated aliphatic-based) radicals, especially alkyl radicals, are especially preferred.

Among the preferred monoamines useful in the method of this invention are aliphatic monoamines such as those of the general formula HNR$^1$R$^2$, wherein R$^1$ is an alkyl radical preferably containing up to ten carbon atoms and R$^2$ is hydrogen or an alkyl radical preferably containing up to ten carbon atoms. Another useful class of monoamines are aromatic monoamines such as those of the general formula HNR$^3$R$^4$, wherein R$^3$ is a phenyl, alkylated phenyl, naphthyl or alkylated naphthyl radical of up to ten carbon atoms and R$^4$ is a hydrogen atom, an alkyl radical preferably containing up to 10 carbon atoms, or R$^2$. Representative examples of these two classes of monoamines are ethylamine, diethylamine, n-butylamine, di-n-butylamine, allylamine, isobutylamine, cocoamine, stearylamine, laurylamine, methyllaurylamine, oleylamine, aniline, methylaniline, N-methylaniline, diphenylamine, benzylamine, tolylamine and methyl-2-cyclohexylamine.

Hydroxy amines are also included in the class of useful monoamines. Such compounds are the hydroxy-hydrocarbyl-substituted analogs of the afore-described monoamines. Preferred hydroxy monoamines have the formulas HNR$^5$R$^6$ and HNR$^7$R$^8$, wherein R$^5$ is an alkyl or hydroxy-substituted alkyl radical of up to 10 carbon atoms, R$^6$ is a hydrogen atom or R$^5$, R$^7$ is a hydroxy-substituted phenyl, alkylated phenyl, naphthyl or alkylated naphthyl radical of up to 10 carbon atoms, and R$^8$ is a hydrogen atom or R$^7$, at least one of R$^5$ and R$^6$ and at least one of R$^7$ and R$^8$ being hydroxy-substituted.

Suitable hydroxy-substituted monoamines include ethanolamine, di-3-propanolamine, 4-hydroxybutylamine, diethanolamine, N-methyl-2-propylamine, 3-hydroxyaniline, N-hydroxyethylethylene diamine, N,N-di(hydroxypropyl)propylene diamine, tris(hydroxymethyl)methylamine, etc. While in general, hydroxy amines containing only one hydroxy group will be employed as reactants, those containing more can also be used.

Heterocyclic amines are also useful in the method of this invention, particularly those that contain a primary or secondary amino group. The heterocyclic ring can incorporate unsaturation and can be substituted with hydrocarbon radicals such as alkyl, alkenyl, aryl, alkaryl or aralkyl. In addition, the ring can contain other hetero atoms such as oxygen, sulfur or other nitrogen atoms, including those not having hydrogen atoms bonded to them. Generally, these rings have 3–10, preferably 5 or 6, ring members. Among such heterocycles are aziridines, azetidines, azolidines, pyridines, pyrroles, piperidines, imidazoles, indoles, piperazines, isoindoles, purines, morpholines, thiamorpholines, N-aminoalkyl morpholines, N-aminoalkyl thiamorpholines, azepines, azocines, azonines, azecines and tetrahydro-, dihydro- and perhydro-derivatives of each of the above. Preferred heterocyclic amines are the saturated ones with 5- and 6-membered rings, especially the piperidines, piperazines and morpholines described above.

Polyamines, particularly aliphatic polyamines, corresponding in general to the aforementioned monoamines are especially preferred in the method of this invention. Among the polyamines are alkylene polyamines (and mixtures thereof) including those having the formula

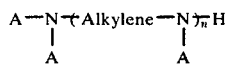

wherein n is an integer between about 1 and 10, preferably between 2 and 8; each A is independently a hydrogen atom or a hydrocarbon or hydroxy-substituted hydrocarbon radical having up to about 30 carbon atoms; and "Alkylene" is a divalent hydrocarbon radical having about 1–18 carbons. Preferably A is an aliphatic radical of up to about 10 carbon atoms which may be substituted with one or two hydroxy groups, and "Alkylene" is a lower alkylene radical having 1–10, preferably 2–6, carbon atoms. Especially preferred are the alkylene polyamines wherein each A is hydrogen. Such alkylene polyamines include methylene polyamines, ethylene polyamines, butylene polyamines, propylene polyamines, pentylene polyamines, hexylene polyamines, heptylene polyamines, etc. The higher homologs of such amines and related aminoalkyl-substituted piperazines are also included. Specific examples of such polyamines include ethylene diamine, triethylene tetramine, tris(2-aminoethyl)-amine, propylene diamine, trimethylene diamine, hexamethylene diamine, decamethylene diamine, octamethylene diamine, di(heptamethylene)triamine, tripropylene tetramine, tetraethylene pentamine, trimethylene diamine, pentaethylene hexamine, di(trimethylene)triamine, 2-heptyl-3-(2-aminopropyl)imidazoline, 1,3-bis(2-aminoethyl)imidazolidine, 1-(2-aminopropyl)-piperazine, 1,4-bis(2-aminoethyl)piperazine and 2-methyl-1-(2-aminobutyl)piperazine. Higher homologs, obtained by condensing two or more of the above-illustrated alkylene amines, are also useful.

The ethylene polyamines, examples of which are mentioned above, are especially useful for reasons of cost and effectiveness. Such polyamines are described in detail under the heading "Diamines and Higher Amines" in Kirk-Othmer, *Encyclopedia of Chemical Technology*, Second Edition, Vol. 7, pp. 22–39. They are prepared most conveniently by the reaction of an alkylene chloride with ammonia or by reaction of an ethylene imine with a ring-opening reagent such as ammonia. These reactions result in the production of the somewhat complex mixtures of alkylene polyamines, including cyclic condensation products such as piperazines. Because of their availability, these mixtures are particularly useful in the method of this invention. Satisfactory products can also be obtained by the use of pure alkylene polyamines.

Hydroxy polyamines, e.g., alkylene polyamines having one or more hydroxyalkyl substituents on the nitrogen atoms, are also useful in preparing amides of this invention. Preferred hydroxyalkyl-substituted alkylene polyamines are those in which the hydroxyalkyl group has less than about 10 carbon atoms. Examples of such hydroxyalkyl-substituted polyamines include N-(2-hydroxyethyl)-ethylene diamine, N,N'-bis(2-hydroxyethyl)ethylene diamine, 1-(2-hydroxyethyl)-piperazine, monohydroxypropyl-substituted diethylene triamine, dihydroxypropyltetraethylene pentamine and N-(3-hydroxybutyl)tetramethylene diamine. Higher homologs obtained by condensation of the above-illustrated hydroxyalkyl-substituted alkylene amines through amino radicals or through hydroxy radicals are likewise useful.

Also useful as basic nitrogen compounds in the method of this invention are hydrazine and organo-substituted hydrazines of the general formula

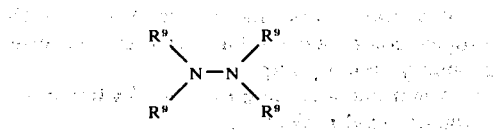

wherein each $R^9$ is independently hydrogen or a $C_{1-30}$ hydrocarbon radical free from acetylenic unsaturation, at least one $R^9$ radical being hydrogen. Preferably, the other $R^9$ radicals are $C_{1-10}$ aliphatic groups. More preferably at least two $R^9$ groups are hydrogen and most preferably at least two $R^9$ groups bonded to the same nitrogen atom are hydrogen and the remaining $R^9$ groups are alkyl groups of up to 10 carbon atoms. Examples of suitable substituted hydrazines are methylhydrazine, N,N-dimethylhydrazine, N,N-dimethylhydrazine, phenylhydrazine, N-phenyl-N'-ethylhydrazine, N-(p-tolyl)-N'-(n-butyl)-hydrazine, N-(p-nitrophenyl)-N-methylhydrazine, N,N'-di(p-chlorophenyl) hydrazine and N-phenyl-N'-cyclohexylhydrazine. Ammonia and amines are, however, preferred in the method of this invention.

As previously noted, the phosphorus-sulfur compounds useful in the method of this invention are those represented by the formula $(RX)_2PSSR'$ wherein $R'$ is hydrogen or R and each R is an aliphatic-based radical. At least one R is a primary radical, and preferably all are primary. When the R radicals are different, it will be readily understood that a mixture of mercaptans is obtained as the product. The R radicals are usually aliphatic hydrocarbon radicals and especially alkyl, particularly those containing about 1–30 and desirably about 5–20 carbon atoms such as octyl, nonyl, decyl, dodecyl, pentadecyl and eicosyl. Mixed phosphorus-sulfur compounds, such as the phosphorodithioic acids prepared by the reaction of phosphorus pentasulfide with a mixture of primary alkanols in the $C_{12-14}$ range, are especially desirable.

The method of this invention is carried out by merely heating the composition consisting essentially of the nitrogen compound and the phosphorus-sulfur compound at a temperature sufficient to result in formation of the mercaptan. Suitable temperatures are usually in the 100°–250° C. range, especially 120°–225° C. It is within the scope of the invention to also have present a substantially inert normally liquid diluent such as kerosene, mineral oil, ethylene glycol monomethyl ether, diethylene glycol monomethyl ether or the like.

When the nitrogen compound is ammonia or a volatile amine such as methylamine, the method is ordinarily carried out under pressure so as to retain all or substantially all of the volatile reagent in the reaction mixture. It is often convenient to heat the reaction mixture to the distillation temperature and to remove the mercaptan by distillation, either at atmospheric or at reduced pressure, as it is formed. Following its removal, the mercaptan may be purified by distillation or the like if desired.

The method of this invention is illustrated by the following examples. All parts are by weight.

EXAMPLE 1

Ethylene diamine, 60 parts (2 equivalents), is added over 15 minutes to 267 parts of a phosphorodithioic acid mixture prepared by the reaction of phosphorus pentasulfide with a commercial mixture of $C_{12-14}$ primary alkanols. An exothermic reaction takes place which causes the temperature to rise from 20° C. to 78° C. The mixture is heated at 156°–209° C. for about one hour as volatile materials (principally unreacted ethylene diamine) are collected by distillation. The distillate is returned to the reaction vessel and the mixture is heated under reflux (190°–200° C.) for an additional 3 hours, cooled and stripped under vacuum at 110° C. The residue separates into two layers and the top layer is removed and filtered. Upon distillation of the filtrate, the desired mercaptan mixture is recovered at 88°–170° C./0.15–0.3 torr.

EXAMPLE 2

A mixture of 2443 parts (4.43 equivalents) of the phosphorodithioic acid of Example 1 and 140 parts of ethylene diamine is prepared; an exothermic reaction causes the temperature to rise to 88° C. The mixture is heated to 173° C. and an additional 95 parts of ethylene diamine is added. After ½ hour of heating at 173°–207° C., additional ethylene diamine is added to a total of 327 parts (10.9 equivalents). Heating is continued for 5 hours at 197°–225° C., after which the mixture is cooled to 90°–110° C. and 1000 parts of water is added. The mixture is heated until the resinous solid which has formed during the reaction is dissolved, and the organic phase is separated and dried under vacuum at 120° C. It is then filtered and distilled and the desired mercaptan is collected at 77°–120° C./0.05–0.08 torr.

EXAMPLE 3

Ethylene diamine, 60 parts (2 equivalents), is reacted with di-n-hexylphosphorodithioic acid at 168°–179° C. During the reaction, unreacted ethylene diamine is recovered by distillation as a low boiling fraction, followed by impure n-hexyl mercaptan. The mercaptan is washed with dilute hydrochloric acid and water, and dried over magnesium sulfate. Upon redistillation, the purified product is collected at 148°–152° C. (atmospheric pressure).

EXAMPLE 4

Following substantially the procedure of Example 2, 401 parts (0.86 equivalent) of the same phosphorodithioic acid is reacted with 127 parts (1.74 equivalents) of n-butylamine. After the addition of water, the organic layer is distilled and the desired mercaptan is collected by distillation.

EXAMPLE 5

Following substantially the procedure of Example 2, 400 parts (0.86 equivalent) of the same phosphorodithioic acid is reacted with 220 parts (1.7 equivalents) of di-n-butylamine. The desired mercaptan is obtained in the same manner.

EXAMPLE 6

Following substantially the procedure of Example 2, 231 parts (0.495 equivalent) of the same phosphorodithioic acid is reacted with 144 parts (1.01 equivalent) of tri-n-propylamine. The desired mercaptan is obtained in the same manner.

EXAMPLE 7 n-Hexylphosphorodithioic acid, 948 parts (3 moles), is heated with 222 parts (1 mole) of phosphorus pentasulfide at 166° C. An exothermic reaction takes place which causes the temperature to rise to 230° C. The reaction mixture is stirred and allowed to cool, and is then heated at 170°–208° C. for 3 hours. During the heating period, a brown solid precipitates. The liquid is decanted and washed with water at 100° C. The organic layer, which comprises the desired tri-n-hexyl tetrathiophosphate, is dried by heating under vacuum.

A mixture of 250 parts (0.69 equivalent) of tri-n-hexyl tetrathiophosphate and 62 parts (2.1 equivalents) of ethylene diamine is heated to 130° C. A solid precipitate forms and 50 parts of mineral oil is added to disperse the solid. The mixture is heated under reflux at 155° C. for 2 hours, with stirring, and the volatile material is then removed by distillation under reduced pressure. The distillate is washed with aqueous hydrochloric acid and with water, and is then dried over magnesium sulfate and distilled. The desired n-hexyl mercaptan is collected at 148°–152° C. (atmospheric pressure).

EXAMPLE 8

One hundred parts of the phosphorodithioic acid of Example 1 is placed in a pressure reactor which is then charged with ammonia until the mixture is neutral to bromphenol blue, sealed and heated carefully at 170°–200° C. for two hours. The reactor is then cooled and vented, and water is added at 100° C. The organic layer is separated and dried by vacuum evaporation, and the desired mercaptan is collected by distillation as in Example 1.

What is claimed is:

1. A method for preparing mercaptans of the formula RSH which comprises heating a composition consisting essentially of at least one of (1) a mixture of a phosphorodithioic acid having the formula $(RO)_2PSSH$, wherein each R is individually an aliphatic radical with at least one R being a primary radical, and a basic nitrogen compound, and (2) a salt of said basic nitrogen compound and said phosphorodithioic acid, at a temperature sufficient to result in formation of said mercaptan.

2. A method according to claim 1 wherein the basic nitrogen compound is ammonia.

3. A method according to claim 2 wherein each R is a primary alkyl radical.

4. A method according to claim 3 wherein the mercaptan is recovered by distillation from the reaction mixture.

5. A method according to claim 1 wherein the basic nitrogen compound contains at least one primary or secondary amino group.

6. A method according to claim 5 wherein each R is a primary alkyl radical.

7. A method according to claim 6 wherein the basic nitrogen compound is an aliphatic amine.

8. A method according to claim 6 wherein the mercaptan is recovered by distillation from the reaction mixture.

9. A method according to claim 8 wherein the amine is an aliphatic amine.

10. A method according to claim 9 wherein the amine contains at least one primary amine group.

11. A method according to claim 10 wherein R contains about 5–20 carbon atoms and the amine is an alkylene polyamine.

12. A method according to claim 11 wherein the amine is an ethylene polyamine.

13. A method according to claim 12 wherein the phosphorodithioic acid is one which may be prepared by the reaction of phosphorus pentasulfide with a mixture of primary alkanols in the $C_{12-14}$ range.

* * * * *